United States Patent [19]

Shimomura et al.

[11] Patent Number: 5,136,274
[45] Date of Patent: Aug. 4, 1992

[54] HUMIDITY SENSOR

[75] Inventors: Tadashi Shimomura, Nagareyama; Hidechika Wakabayashi, Abiko; Yasunobu Shigaki, Katsushika; Mitsuzo Arii, Ohta, all of Japan

[73] Assignee: Mitsubishi Gas Chemical Company, Inc., Tokyo, Japan

[21] Appl. No.: 472,380

[22] Filed: Feb. 1, 1990

[51] Int. Cl.⁵ .............................................. H01C 7/00
[52] U.S. Cl. .................................... 338/35; 73/73
[58] Field of Search ............... 338/35; 73/73, 335, 73/336.5; 324/694; 55/275; 361/286

[56] References Cited

U.S. PATENT DOCUMENTS

| 4,603,372 | 7/1986 | Abadie et al. | 361/286 |
| 4,634,756 | 1/1987 | Mishra et al. | 338/35 X |
| 4,770,923 | 9/1988 | Wasa et al. | 73/73 |
| 4,942,364 | 7/1990 | Nishijima et al. | 338/35 X |

FOREIGN PATENT DOCUMENTS 078058 5/1983 European Pat. Off. .
WO85/01222 3/1985 PCT Int'l Appl. .

Primary Examiner—Marvin M. Lateef
Attorney, Agent, or Firm—Foley & Lardner

[57] ABSTRACT

A chemically and physically stable humidity sensor including a porous sintered body and electrodes, which is formed by bringing a humidity sensor including a porous sintered body and electrodes into contact with a solution of a polyurethane resin.

9 Claims, 1 Drawing Sheet

HUMIDITY SENSOR

FIELD OF THE INVENTION

The present invention relates to a humidity sensor to detect relative humidity as a change in electric resistance.

PRIOR ART OF THE INVENTION

Conventionally known as a humidity sensor are sensors which use an electrolytic salt such as lithium chloride, etc., sensors which make use of a film of an organic polymer such as polyamide, polyethylene, etc., and sensors which use a sintered body of metal oxide such as titanium oxide, aluminum oxide, tin oxide, etc. Concerning these sensors, it is generally said that the metal oxide sintered body is chemically and physically more stable than other organic polymer films, etc., and is the most advantageous.

However, the metal oxide sintered body is, in general, porous, and it has a defect that if a substance such as oil, chemical material, or the like is adsorbed in the pores or on the surface of the sintered body, its surface chemical state or pore state changes and the humidity sensing characteristics thereof also change.

In order to solve the above problem, there is proposed a sensor of metal sintered body which takes advantage of the heat resistance of metal oxide sensors and, therefore, has a heating cleaning unit to improve reliability. There is another example of a sensor in which a water-repellent resin or permeable nonwoven fabric is used in a protective case. However, there are problems that humidity stabilization within the case takes time, etc.

On the other hand, in a humidity sensor using an organic polymer film, its humidity sensing material is covered with a protective film in order to prevent various adsorbed substances from deteriorating the humidity sensing characteristics. However, this sensor has a defect that its humidity sensing material film is peeled off due to water droplets formed by dew condensation or water vapor droplets generated from a humidifier, and as a result, the sensor fails to work as such.

SUMMARY OF THE INVENTION

It is an object of the present invention to provide an improved humidity sensor of which the humidity sensing characteristics do not change.

It is another object of the present invention to provide an improved humidity sensor which is chemically and physically stable.

It is further another object of the present invention to provide an improved humidity sensor of which the humidity sensing characteristics do not change even under an environment containing water and vapor water droplets, oil and oil vapors, organic acids, inorganic corrosive gases, cigarette smoke, aldehydes, etc.

According to the present invention, there is provided an improved humidity sensor comprising a porous sintered body and electrodes, which is formed by bringing a humidity sensor comprising a porous sintered body and electrodes into contact with a solution of a polyurethane resin.

DETAILED DESCRIPTION OF THE INVENTION

Figure 1:
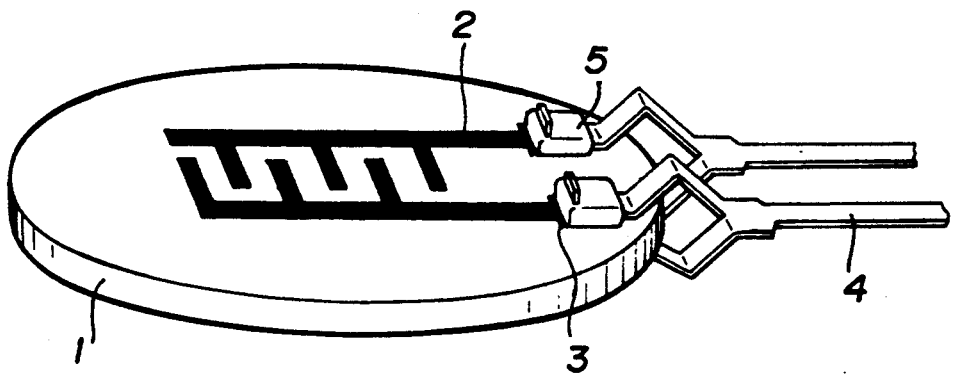
FIGURE 1 shows a perspective view of a porous ceramic humidity sensor.

The scope of the humidity sensor comprising a porous sintered body and electrodes in the present invention includes both a humidity sensor having a volume resistance which changes with a humidity change and a humidity sensor having a surface resistance which changes with a humidity change.

The porous sintered body usable in the present invention is known per se, and is produced by firing a metal compound or its mixture with a metal salt, or the like in air at temperatures to be discussed later. Examples of the metal compound include oxides such as $MgO$, $TiO_2$, $ZrO_2$, $Nb_2O_5$, $TaO$, $Ta_2O_5$, $Cr_2O_3$, $MoO_3$, $WO_3$, $MnO_2$, $Mn_3O_4$, $FeO$, $Fe_2O_3$, $CoO$, $Ca_2O_3$, $NiO$, $Ni_2O_3$, $Ni_3O_4$, $ZnO$, $Al_2O_3$, $Ga_2O_3$, $In_2O_3$, $Tl_2O_3$, $SiO_2$, $GeO_2$, $SnO$, $SnO_2$, $PbO$, $Sb_2O_3$, $Bi_2O_3$, etc., compound oxides such as $Mg_2Fe_2O_4$, $ZnFe_2O_4$, $MgAl_2O_4$, $MgCrO_3$, $ZnCrO_3$ (these compound oxides are spinel), $3Al_2O_3 \cdot 2SiO_2$ (Mullite), $SiO_2 \cdot MgO$, etc., and the like. Among these, $TiO_2$, $\gamma\text{-}Al_2O_3$, $ZnO$, $MgO$, $ZrO_2$, $NiO$, $MgAl_2O_4$, etc., are particularly desirable. Examples of the above "metal salt or the like", which is mixed with these metal compounds, include alkali metal salts such as sodium chloride, potassium chloride, etc., alkali metal oxides such as sodium oxide, etc., alkaline earth metal hydroxides such as calcium hydroxide, etc., and the like.

The porous sintered body may be produced according to the following production technique applied to the production of usual ceramics.

First, the components (materials) for the sintered body are weighed out, and then, they are fully mixed in a ball mill, a shaker mill, or the like by a dry method or a wet method using a mixed solvent of water, methyl alcohol, etc. Thereafter, the resultant mixture is optionally dried, calcined at a suitable temperature, and then crushed to obtain a raw material powder. This raw material powder in an ascrushed state may be molded by a dry method, or it may be kneaded with a binder, e.g. polyvinyl alcohol, polyethylene glycol, etc., dried and shaped. This molded body is sintered in air to give a sintered body. In general, the sintered body preferably has a porous structure in which the porosity is 10 to 55 % and the pore diameter is not more than 1 $\mu$m. The sintered body used in the present invention can be obtained by setting conditions as follows: the raw material powder has a diameter of 0.1 to 3 $\mu$m, the molding pressure is 50 to 1,000 kg/cm$^2$, the sintering temperature is 500 to 1,200° C., and the sintering time is 0.5 to 3 hours.

The sintered body obtained as above is polished as required, and then a conventional paste such as gold paste, platinum paste, ruthenium paste, or the like is applied to form electrodes, whereby a humidity sensor is produced.

The urethane resin is brought into contact with the humidity sensor by immersing the humidity sensor in a solution of a urethane resin, or spraying the humidity sensor with the urethane resin solution, and then drying it. The solvent for the urethane resin does not need to be one which can dissolve the resin entirely. That is, even if a solvent is used which only partially disolves the resin, the humidity sensor can be surface-treated by immersing the humidity sensor in the resin-dissolved portion. Typical examples of the solvent are dimethylformamide, toluene, tetrahydrofuran, etc. The solution concentration is a factor in determining the size and depth of the pores of the treated humidity sensor, and the concentration of the urethane resin is desirably 1 to 5% by weight in view of the pore state and humidity sensing characterisics. The time for immersing the porous sintered body is desirably not less than 10 seconds, during which the sintered body can be degassed.

The polyurethane resin is a high-molecular compound having a urethane bond in its main chain-constituting unit (or recurring unit), and is usually obtained by a reaction between a diisocyanate and polyhydric alcohol.

As the diisocyanates, both aromatic diisyanates and aliphatic diisocyanates are usable. Examples of the diisocyanate include tolylene diisocyanate, 3,3'-bitolylene-4,4'-diisocyanate diphenylmethane-4,4'-diisocyanate, 3,3'-dimethyl-diphenylmethane-4,4'-diisocyanate, m-phenylene diisocyanate, dicyclohexamethane diisocyanate, trimethylene diisocyanate, tetramethylene diisocyanate, pentamethylene diisocyanate, hexamethylene diisocyanate, octamethylene diisocyanate, naphthalene-1,5-diisocyanate, isophorone diisocyanate, etc.

Examples of the polyhydric alcohol include tetramethylene glycol, hexamethylene glycol, octamethylene glycol, cyclohexane glycol, etc., and further, they also include polyethylene glycol, polytetraethylene glycol, polyoxypropylene glycol, polyether glycol such as polyoxypropylene-polyoxyethylene glycol, and polyester glycol typified by a condensate of adipic acid with ethylene glycol. Among these, the polyether glycol is preferable use.

FIGURE 1 is a perspective view showing one embodiment of an improved humidity sensor using a porous sintered body, provided by the present invention, in which a disk-shaped porous sintered body 1 has comb-like electrodes 2 bonded thereto by baking, and each of the electrodes 2 is connected, through an electrode pad 3 and by soldering 5, to a lead frame 4.

The humidity sensor of the present invention exhibits excellent adherence between the polyurethane resin on the surface of the porous sintered body and the porous sintered body, and deterioration of the humidity sensing characteristics is prevented owing to the presence of the polyurethane resin.

According to the present invention, there is provided a humidity sensor with humidity sensing characteristics which change little even under an environment containing water and vapor water droplets, oil and oil vapor, organic acids, inorganic corrosive gases, cigarette smokes, aldehydes, etc.

EXAMPLES

The present invention will be explained hereinbelow by reference to Examples. Durability tests in the Examples were carried out as follows.

(1) Water resistance test (i) Immersing test

A sensor sample was immersed in distilled water for 60 minutes, and then air-dried.

(ii) Water droplets spray test

A humidifier was used to spray a sensor sample with mist-like water droplets for 30 minutes, and the spraying was stopped for 30 minutes. This procedure was repeated over 3 days.

(2) Oil test (i) A sensor sample was immersed in salad oil for 10 seconds, and the surface of the sample was lightly wiped with paper.

(ii) Steam test

Salad oil was allowed to smoke at 200° C., and a sample sensor surface was exposed to the smoke.

(3) Organic acid test

A sample sensor was placed under an atmosphere saturated with rice vinegar.

(4) Inorganic corrosive gas test

A sample sensor was placed in an atmosphere containing 2,000 ppm of $SO_2$ or $H_2S$.

(5) Cigarette smoke test

Three cigarettes were smoked in a 20-liter desiccator, and a sample sensor was placed therein.

(6) Aldehyde test

A sample sensor was left to stand in a formaldehyde-saturated steam for 24 hours.

In the following Examples, "%" stands for "% by weights".

EXAMPLE 1

A powder was prepared by mixing $TiO_2$, $CuO_2$ and $Na_2CO_3$ in a mixing ratio of 10:2:1 (by weight), and 50 g of his powder was put into an automatic mortar. While the powder was mixed, 20 ml of 8% polyvinyl alcohol aqueous solution as a binder was added gradually, and then the powder was sufficiently mixed for 45 minutes. The resultant mixture was then granulated in a 40 mesh sieve, and dried at 80° C. for 1 hour. This raw material powder was molded under a pressure of 500 kg/cm$^2$ to form a disk-shaped body having a diameter of 7 mm and a thickness of 0.8 mm.

The disk-shaped body was sintered at 900° C. for 3 hours to give a sintered body. A gold-platinum-palladium paste was printed on one surface of the porous sintered body and baked at 850° C. for 10 minutes to form comb-like electrodes as shown in FIGURE 1. Then, lead frames were attached to the terminal pad portions of the electrodes, and soldered to give a humidity sensor.

The humidity sensor was immersed in a solution of a polymer of polytetramethylene glycol with tolylene diisocyanate (trade name: PC-110, supplied by Mitsubishi Chemical, Ltd.) in toluene (urethane concentration: 3%) for 10 seconds, and preliminarily heated at 80° C. for 10 minutes. Then, the humidity sensor was heated at 120° C. for 30 minutes, The above procedure was repeated to prepare the same humidity sensors as above for durability tests.

Table 1 shows the results of the durability tests of the above sensors treated with urethane resin and sensors treated with no urethane resin.

TABLE 1

| | Resistance (kΩ) at 60% RH | | | |
| | Sensors treated with urethane resin | | Sensors treated with no urethane resin | |
| Test | before | after | before | after |
| --- | --- | --- | --- | --- |
| (1) Water resistance test | | | | |
| (i) Immersing | 75 | 75 | 40 | 65 |
| (ii) Water droplets spray | 90 | 98 | 40 | 50 |
| (2) Oil test | | | | |
| (i) Immersing | 90 | 90 | 39 | 51 |
| (ii) Steam | 80 | 89 | 38 | 100 |
| (3) Organic acid test Rice vinegar | 55 | 55 | 38 | 49 |
| (4) Inorganic corrosive gas test | | | | |
| $SO_2$ gas (2,000 ppm) | 94 | 95 | 39 | 90 |
| $H_2S$ gas (2,000 ppm) | 130 | 170 | 41 | 180 |
| (5) Cigarette smoke | 100 | 120 | 40 | 56 |

TABLE 1-continued

|  | Resistance (kΩ) at 60% RH | | | |
|---|---|---|---|---|
|  | Sensors treated with urethane resin | | Sensors treated with no urethane resin | |
| Test | before | after | before | after |
| test | | | | |
| (6) Aldehyde test | 68 | 75 | 39 | 67 |

EXAMPLE 2

Example 1 was repeated except that $TiO_2$, $Sb_2O_3$, and $LiO_2$ (weight ratio: 10:2:1) were used in place of $TiO_2$, $CU_2O$ and $Na_2CO_3$ (weight ratio: 10:2:1) and that there were used a solution of a polymer of polytetramethylene glycol with tolylene diisocyanate (trade name: PC-110, supplied by Mitsubishi Chemical, Ltd. ) in tetrahydrofuran (urethane concentration: 2.5%) in place of that used in Example 1. Table 2 shows the results of the durability tests of the resultant sensors treated with urethane resin and sensors treated with no urethane resin.

TABLE 2

|  | Resistance (kΩ) at 60% RH | | | |
|---|---|---|---|---|
|  | Sensors treated with urethane resin | | Sensors treated with no urethane resin | |
| Test | before | after | before | after |
| (1) Water resistance test Water droplets spray | 65 | 68 | 35 | 150 |
| (2) Oil test Steam | 70 | 78 | 32 | 85 |
| (3) Organic acid test Rice vinegar | 68 | 65 | 38 | 105 |
| (4) Inorganic corrosive gas test $SO_2$ gas (2,000 ppm) | 72 | 70 | 30 | 78 |
| (5) Cigarette smoke test | 79 | 75 | 34 | 56 |
| (6) Aldehyde test | 67 | 75 | 28 | 59 |

EXAMPLE 3

Example 1 was repeated except that $Na_2TeO_3$ was used in place of $Na_2CO_3$ and that there was used a solution of a polymer of a mixture of polytetramethylene glycol and polyethylene glycol with a mixture of dicyclohexamethane-4,4'-isocyanate and isophorone diisocyanate (trade name: PC-200, supplied by Mitsubishi Chemical, Ltd.) in dimethylformamide (urethane concentration: 4%) in place of that used in Example 1. Table 3 the results of the durability tests of the resultant sensors treated with urethane resin and sensors treated with no urethane resin.

TABLE 3

|  | Resistance (kΩ) at 60% RH | | | |
|---|---|---|---|---|
|  | Sensors treated with urethane resin | | Sensors treated with no urethane resin | |
| Test | before | after | before | after |
| (1) Water resistance test Water droplets spray | 55 | 58 | 45 | 170 |
| (2) Oil test Steam | 60 | 68 | 42 | 95 |
| (3) Organic acid test Rice vinegar | 48 | 55 | 43 | 145 |
| (4) Inorganic corrosive gas test $SO_2$ gas (2,000 ppm) | 55 | 58 | 43 | 88 |
| (5) Cigarette smoke test | 59 | 55 | 44 | 66 |
| (6) Aldehyde test | 62 | 65 | 48 | 79 |

What is claimed is:

1. A improved humidity sensor comprising a porous sintered body having an electrical resistance which changes with changes in humidity, at least two spaced electrodes arranged on said sintered body, and a surface film of a polyurethane resin formed thereon by contacting said porous sintered body and electrodes with a solution of a polyurethane resin.

2. An improved humidity sensor according to claim 1, wherein the humidity sensor comprising a porous sintered body and electrodes is brought into contact with the solution of a polyurethane resin by immersing the humidity sensor in the solution of a polyurethane resin or by spraying the humidity sensor with the solution of a polyurethane resin.

3. An improved humidity sensor according to claim 1, wherein the solution of a polyurethane resin has a polyurethane concentration of 1 to 5% by weight.

4. An improved humidity sensor according to claim 2, wherein the humidity sensor comprising a porous sintered body and electrodes is immersed in the solution of a polyurethane resin for not less than 10 seconds.

5. An improved humidity sensor according to claim 1, wherein the polyurethane resin is a reaction product between a diisocynate and a polyhydric alcohol.

6. An improved humidity sensor according to claim 1, wherein the porous sintered body is formed mainly of a metal oxide.

7. An improved humidity sensor according to claim 6, wherein the porous sintered body is formed by sintering the metal oxide in air.

8. An improved humidity sensor according to claim 6, wherein the porous sintered body is formed by sintering a mixture of the metal oxide with a metal salt in air.

9. An improved humidity sensor according to claim 1, wherein the porous sintered body has a film of a polyurethane resin formed on the surface and pores thereof.

* * * * *